United States Patent [19]

Simpson et al.

[11] Patent Number: 4,781,186

[45] Date of Patent: Nov. 1, 1988

[54] ATHERECTOMY DEVICE HAVING A FLEXIBLE HOUSING

[75] Inventors: John B. Simpson, Woodside; Hira Thapliyal, Mountain View; Hanson S. Gifford, III, Palo Alto; Tommy G. Davis, Mountain View, all of Calif.

[73] Assignee: Devices for Vascular Intervention, Inc., Redwood City, Calif.

[21] Appl. No.: 80,342

[22] Filed: Jul. 31, 1987

Related U.S. Application Data

[63] Continuation-in-part of Ser. No. 834,947, Feb. 28, 1986, abandoned, and a continuation-in-part of Ser. No. 732,641, May 10, 1985, abandoned, which is a continuation-in-part of Ser. No. 615,298, May 30, 1984, abandoned.

[51] Int. Cl.⁴ ............................................ A61B 17/32
[52] U.S. Cl. .................................................... 128/305
[58] Field of Search ............... 128/305, 751, 752, 753, 128/754, 755; 604/22

[56] References Cited

U.S. PATENT DOCUMENTS

| 1,677,337 | 7/1928 | Grove | 128/305.1 |
| 3,173,414 | 3/1965 | Guillant | 128/752 |
| 3,561,429 | 2/1971 | Jewett et al. | 128/305 |
| 3,606,878 | 9/1971 | Kellogg | 128/753 |
| 3,844,272 | 10/1974 | Banko | 128/305 |
| 4,111,207 | 9/1978 | Seiler | 128/305 |
| 4,513,745 | 4/1985 | Amoils | 128/305 |
| 4,669,469 | 6/1987 | Gifford et al. | 128/305 |
| 4,685,458 | 8/1987 | Leckrone | 128/305 |

FOREIGN PATENT DOCUMENTS 2804015 8/1979 Fed. Rep. of Germany ...... 128/305

Primary Examiner—Charles J. Myhre
Assistant Examiner—David A. Okonsky
Attorney, Agent, or Firm—Flehr, Hohbach, Test, Albritton & Herbert

[57] ABSTRACT

An atherectomy device having a housing at the distal end of a catheter adapted for insertion into the vascular system. The housing has a cutout in one side, and a cutter that is mounted in the housing for both axial and rotary movement with respect to the cutout. At least a portion of the housing is formed of a material which permits bending of the housing as it follows the contours of the vessel. The housing is also adapted to retain the severed atheroma materials.

14 Claims, 2 Drawing Sheets

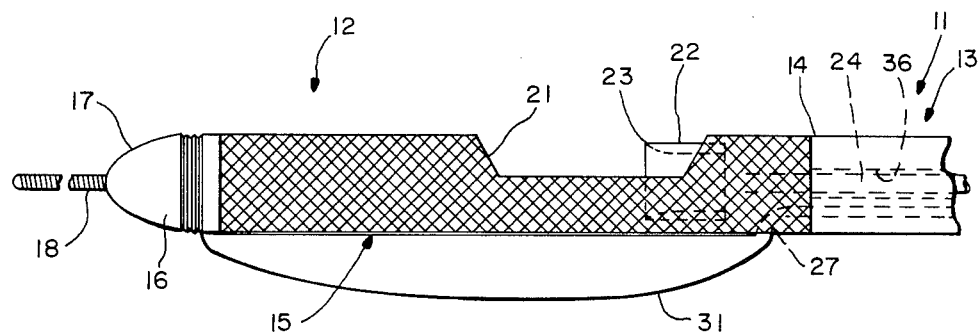
FIG.—1
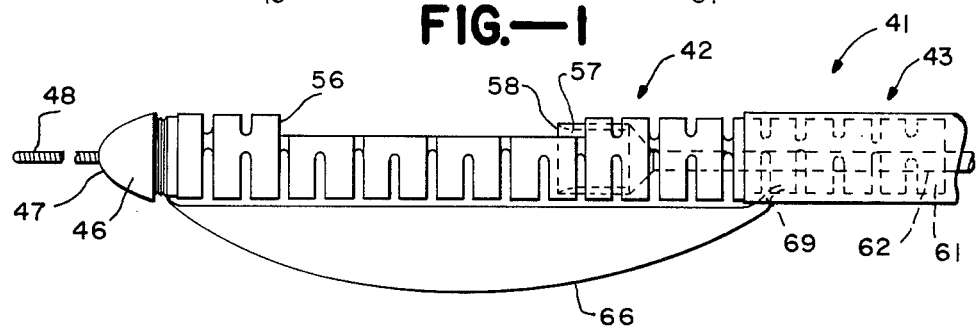
FIG.—2
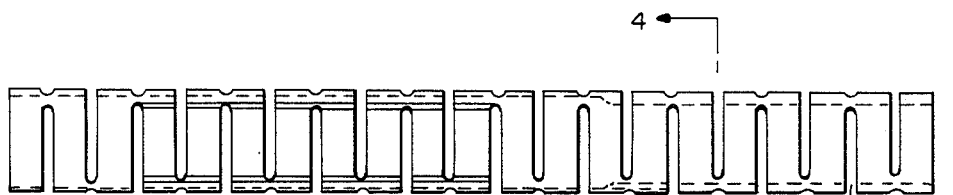
FIG.—3
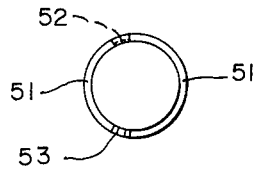
FIG.—4
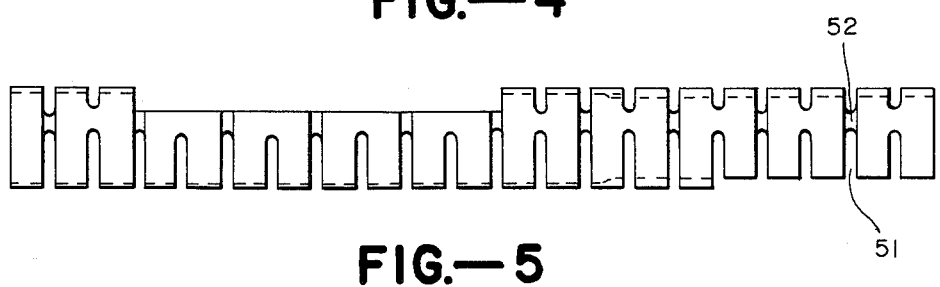
FIG.—5

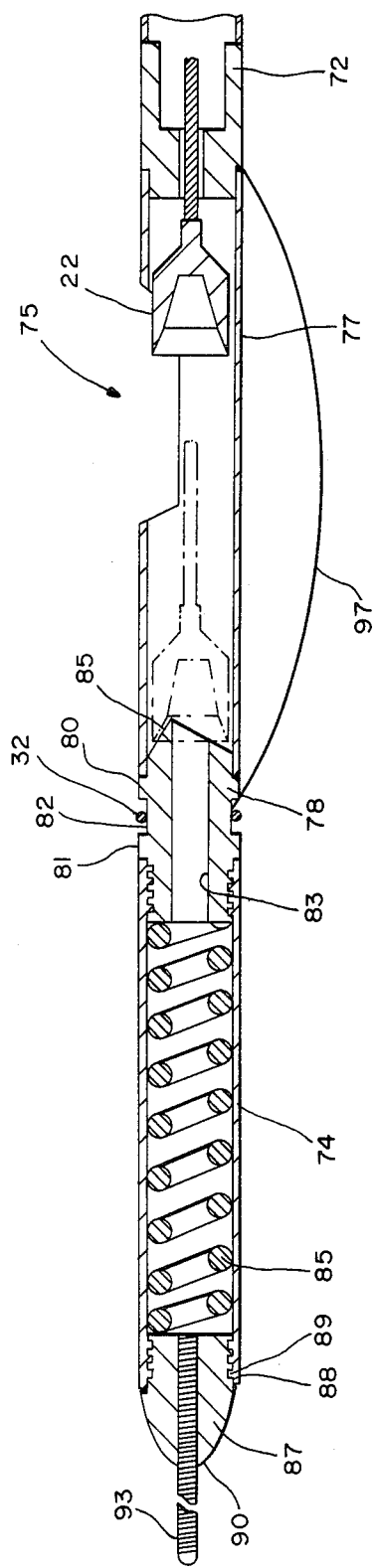
FIG.—6
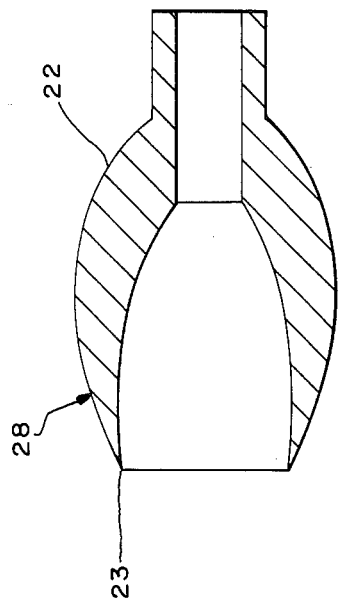
FIG.—7

ATHERECTOMY DEVICE HAVING A FLEXIBLE HOUSING

This application is a continuation-in-part of copending application Ser. No. 834,947 filed Feb. 28, 1986 and co-pending application Ser. No. 732,641 filed May 10, 1985, which was a continuation-in-part of application Ser. No. 615,298 filed May 30, 1984, now abandoned.

This invention relates to an atherectomy device and more particularly, to an atherectomy device having a flexible housing.

Atherectomy devices have heretofore been provided such as disclosed in co-pending application Ser. No. 732,691 filed on May 10, 1985. Such atherectomy devices in the past have utilized rigid housing structures with collection chambers having a length ranging from ½ inch to 1 inch. Rigidity through such a length is not objectionable where the vessels in which the device is being utilized is relatively straight and non-tortuous. However, difficulties arise with the use of such a rigid housing when smaller coronary vessels are encountered where it is necessary to follow the tortuousity of the vessels. There is therefore a need for an atherectomy device housing at least a part of which is flexible. In addition there is a need for an atherectomy device which has a larger collection chamber to eliminate the need for repeated removals and insertions of the atherectomy device.

In general it is an object of the present invention to provide an atherectomy device having a housing at least a portion of which is flexible.

Another object of the invention is to provide a device of the above character in which the housing can be provided with a cut-out.

Another object of the invention is to provide a device of the above character in which an inflatable balloon may be carried by the housing in a region opposite the cutout in the housing.

Another object of the invention is to provide a device of the above character in which a braided type construction can be utilized for the flexible portion of the housing.

Another object of the invention is to provide a device of the above character in which the cutter is retained within the braided-type housing.

Another object of the invention is to provide a device of the above character in which the housing generally retains its desired shape when passing through bends.

Another object of the invention is to provide a device of the above character in which the housing will not kink or tend to fold over as it bends in passing around curves in passages being navigated.

Another object of the invention is to provide a device of the above character in which the atheroma materials removed are retained within an internal collection chamber in the housing.

Another object of the invention is to provide a device of the above character in which the collection chamber is provided in a flexible portion of the housing.

Another object of the invention is to provide a device of the above character in which the housing includes a non-dulling cutter stop.

Additional objects and features of the invention will appear from the following description in which the preferred embodiments are set forth in detail in conjunction with the accompanying drawing.

FIG. 1 is a side elevational view of a portion of an atherectomy device having a flexible housing and incorporating the present invention and utilizing a braided construction.

FIG. 2 is a side elevational view similar to FIG. 1 of an atherectomy device having a flexible housing in which the housing is formed of a rigid material but which is cut in such a manner so as to permit flexing of the housing as the housing passes through a tortuous vessel.

FIG. 3 is a side elevational view of an elongate tube formed to provide the housing which is shown in FIG. 2.

FIG. 4 is a cross sectional view taken along the line 4—4 of FIG. 3.

FIG. 5 is a top plan view of the elongate tube shown in FIG. 3.

FIG. 6 is a cut-away side view of an alternative embodiment of the atherectomy device incorporating a rigid cutter tube portion.

FIG. 7 is a cut-away side view of a rounded-tip cutter.

In general, the atherectomy device having a flexible housing of the present invention is comprised of a flexible tubular member having proximal and distal ends and having at least one lumen extending therethrough. A housing is secured to the distal end of the tubular member. The housing is provided with a cutout in one side thereof which faces in a direction generally perpendicular to the longitudinal axis of the housing. A collection chamber is formed within the housing to retain severed atheroma materials within the body of the housing. A rotary cutter is movably mounted in the housing for movement longitudinally of the housing through the cutout and into the collection chamber. At least a portion of the housing is formed of a flexible material so as to permit bending of the housing as it follows the contours of a vessel. The entire housing may be flexible or alternatively the portion of the housing serving as a collection chamber may be flexible. An inflatable balloon means is carried by the housing on the side opposite the cutout. The inflatable balloon means is mounted such that when inflated, it causes the cutout to move towards the sidewall of the vessel.

More particularly, as shown in FIG. 1 of the drawings, the atherectomy device 11 having a flexible housing 12 includes an elongate flexible tubular member 13. The tubular member 13 can be of a multiple lumen type such as described in co-pending application Ser. No. 732,691 filed on May 10, 1985, or alternatively, can be a single lumen tubular member such as that described in co-pending application Ser. No. 834,950, filed Feb. 28, 1986. The tubular member 13 is provided with proximal and distal extremities with the distal extremity 14 being shown in FIG. 1. The proximal extremity of the housing 12 is secured to the distal extremity of the tubular member 13.

The flexible housing 12 as shown in FIG. 1 is of a braided type construction. The flexible housing 12 is formed by braiding fibers in at least a single layer braid and then coating the fibers and filling the interstices between the braided fibers to increase the strength of the braided tube or tubing 15. Thus by way of example, the braided tube can be formed of suitable fibers, such as of stainless steel having a thickness ranging from two mils to three mils and preferably having a thickness of approximately 2.5 mils. Thereafter, the stainless steel fibers can be coated with a plastic such as polyurethane by dipping the fibers into polyurethane. The polyurethane is permitted to dry and harden to provide a generally cylindrical tube 15 which holds its shape while still being flexible. One end of the tube 15 is secured to the distal extremity of the tubular member 13. The braided tube 15 is then cut to a suitable length and a nose member 16 is mounted in the distal extremity of the braided member 15 forming the housing 12. The nose member or cone 16 is provided with a rounded outer surface 17. A fixed flexible spring-like guide wire 18 is mounted in the nose and extends through the surface 17. The housing 12 is provided with a cutout 21 which can be formed in a suitable manner such as by the use of a laser or grinder. The cutout 21 is disposed in a side wall of the flexible housing 12 and covers less than one-half the circumference of the housing. The cutout 21 generally faces in a direction which is perpendicular to the longitudinal axis of the housing. The portion of tube 15 positioned distally of cutout 21 forms collection chamber 29 which serves to retain severed portions of the atheroma. The length of collection chamber 29 may be readily varied dependent upon the size of the occlusions that are expected to be encountered.

A cutter 22 is disposed in the housing 12 and is provided with a circular cutting edge 23 which lies in a plane perpendicular to the longitudinal axis of the housing 12. The cutter 22 may be either substantially cylindrical as seen in FIG. 1, or may incorporate a rounded tip 28 that tapers toward the leading cutting edge 23 of cutter 22. A representative rounded tip cutter geometry is shown in FIG. 7. The rounded tip facilitates cutting while the housing 12 is in a curved position. Without such a cutter design, there is a danger of the cutter 22 cutting into the wall of the cutout 21 within housing 12 as it completes the cutting stroke. The actual geometry of the cutter's taper will vary dependent upon the atherectomy catheter's expected use. particularly, if the region of cutout 21 is expected to be relatively straight, a cylindrical cutter may be used. However, as the anticipated curvature of the region of cutout 21 increases, so should the curvature of the rounded tip 28 of cutter 22.

The cutter 22 is secured to a flexible driving cable 24 which extends through a lumen 26 provided in the tubular member 13. Means (not shown) is provided for rotating the flexible driving cable 24 such as that disclosed in co-pending application Ser. No. 732,691 filed on May 10, 1985 and in co-pending application Ser. No. 834,743, filed Feb. 28, 1986 and which also permits advancement and retraction of the cutter 22 with respect to the cutout 21.

Means is provided for urging the cutout 21 of the housing 12 into an atheroma to be removed by the use of the atherectomy device and consists of an inflatable balloon 31 which is secured exterior of the housing on the side opposite the housing in which the cutout 21 is provided. The distal extremity of the balloon is secured to the nose member 16 by suitable means such as nylon wire 32 which is wrapped into an annular recess 33. The nylon wire wrap 32 is fastened in place by use of a suitable plastic such as cyanoacrylate. The rear extremity of the balloon 31 extends through a small hole 27 provided in the flexible housing 12 and is placed in communication with the lumen 36 provided in the tubular member 13 to permit the balloon 31 to be inflated and deflated.

Operation and use of the atherectomy device shown in FIG. 1 is very similar to that described for the operation of the atherectomy devices in co-pending application Ser. No. 732,691, filed on May 10, 1985. The principal difference, however, is that because of the flexible nature of the housing 12, the atherectomy device can readily follow the contours of a vessel. This is particularly advantageous with smaller vessels in the human body such as the coronary arteries associated with the heart. Even though the flexible housing may be bent, it is still possible to operate the cutter 22 and to advance and retract the cutter to remove an atheroma or portions of an atheroma in a vessel. The cutout 21 is sized in such a manner so that even though the housing itself is quite flexible, the cutter 22 will not become dislodged from the housing. Even though the housing 12 is quite flexible, it still will retain its shape in going around bends and will not kink or tend to fold over.

The construction of the flexible housing 12 is such as to make it possible to make housings of a very small diameter. Thus by way of example, housings of a 5 French size and even as small as a 3 French size can be made. Flexible housings of this type are particularly advantageous when working with small vessels in the human body as, for example, associated with the heart, kidney and the like.

Another embodiment of the atherectomy device having a flexible housing is shown in FIG. 2. The atherectomy device 41 shown therein has a flexible housing 42. The device consists of a tubular member 43 much like the tubular member 13 in the previous embodiment which can be provided with a single lumen or alternatively, with multiple lumens extending from the proximal to the distal ends thereof. The housing 42 is secured to the distal extremity of the tubular member 43. A nose member 46 is mounted in the distal extremity of the housing 42 and is provided with a rounded surface 47 having a flexible helical spring guide wire 48 extending forwardly therefrom. The housing 42 can be formed of a relatively rigid plastic or metal. As for example, it can be formed of stainless steel.

In order to impart flexibility to the housing 42, a plurality of spaced apart arcuate cutouts 51 are provided. As can be seen from FIGS. 3, 4 and 5, the cylindrical tubing from which the housing is fabricated is provided with spaced apart parallel arcuate slots 51 along the longitudinal axis of the tubing or housing. The slots 51 may extend at an angle which is substantially perpendicular to the longitudinal axis of the tubing as shown in the drawings. Alternatively they could be arranged such that they slant up to 45 degrees from a vertical axis perpendicular to the longitudinal axis of the tubing. As shown, particularly in FIG. 4, interconnecting portions 52 and 53 are provided to retain the integrity of the tubing. By way of example, these portions 52 and 53 can subtend approximately 20° and are spaced approximately 10° from a vertical centerline passing through the longitudinal axis of the tubing. The tubing forming the housing 42 can have a wall thickness ranging from approximately 0.003 to 0.015 inches and preferably having a thickness of approximately 0.005 inches.

From the foregoing it can be seen that a substantially Z-shaped pattern is provided which extends longitudinally of the housing. The cutouts can have a suitable width such as 0.010 inches and the housing 42 can have suitable overall length as, for example, approximately 1 inch. The Z-type pattern provided in the housing 42 makes it possible to bend the housing in various directions much in the same way as a spring to provide a spring-type motion so that the housing 42 can follow the contours of an arterial vessel much in the same way as the flexible housing 12 shown in FIG. 1.

The housing 42 is provided with a cutout 56 extending longitudinally of the housing and disposed in one side of the housing and facing outwardly in a direction which is perpendicular to the longitudinal axis of the housing. A cutter 57 is disposed within the housing 42 and is provided with a circular cutting edge 58 which extends at right angles to the longitudinal axis of the housing 42. A flexible drive cable 61 is secured to the housing and is disposed in a lumen 62 provided in the tubular member 43 so that the cutter 57 can be rotated and advanced and retracted much in the same way as the cutter 22 shown in FIG. 1. An inflatable balloon 66 is carried by the housing 42 and is disposed on the exterior of the housing on the side of the housing opposite the cutout 56 and has one extremity of the same secured to the nose piece 46 by nylon wire 67 which is disposed in an annular recess 68 provided in the nose. As with the previous embodiment, the nylon wire wrap can be coated with a suitable plastic such as cyanoacrylate. The other extremity of the balloon passes through an opening 69 provided in the housing 42 and is in communication with the lumen 62 so that the balloon can be inflated and deflated in the same manner as the balloon 31.

In order to impart additional strength to the housing, it is desirable to place a thin flexible plastic material such as a polyurethane or a polyamid in the arcuate cutouts 51. This thin material is very strong but can be flexed readily so as to not inhibit the flexibility of the housing while still giving considerable strength to the housing whereby the housing will retain its desired tubular configuration.

Operation of this embodiment of the atherectomy device with a flexible housing is substantially identical with that hereinbefore described. The housing 42 has substantially the same flexibility capabilities as does the housing 12 shown in the embodiment in FIG. 1.

Still another embodiment of the atherectomy device incorporating the present invention is shown in FIGS. 6 and 7. As shown therein, the housing 71 of the atherectomy device is provided with a tailpiece 72, a cutter tube 77, a rigid cutter stopper 78, an elongate flexible collection chamber 74 and a nose cone 87. The proximal end of cutter tube 77 is secured to the distal extremity of the tubular member 13 through tailpiece 72. The nose cone 87 has a rounded outer surface 90 that caps the distal end of the collection chamber 74. A fixed flexible spring-like guide wire 93 mounted to nose cone 87, extends distally from the surface 90. A substantially cylindrical annular cutter 22 may be disposed within the cutter tube 77 in the same manner as cutter 22 was disposed within housing 12 as described with respect to FIG. 1.

This embodiment, differs from that shown in FIG. 1 primarily in that the housing includes a cutter tube portion 77 and a cutter stopper 78. Cutter tube 77 includes a cutout 75 disposed in a side wall. By way of example, the cutter tube 77 may be rigid and formed of stainless steel. Cutter stopper 78 is substantially tubular and is sized and shaped to be tightly received by cutter tube 77 and collection chamber 74. A pair of annular ribs 80 and 81 have the same external diameter as cutter tube 77 and collection chamber 74 respectively. The gap 82 between ribs 80 and 81 provides a foundation onto which a balloon 97 may be tied. An annular shoulder 83 protrudes from the proximal end of cutter stopper 78. Shoulder 83 is adapted to limit the distal movement of cutter 22 and is tapered to protect the cutting edge 23 of cutter 22. It also allows any atheroma materials severed during the cutting step to feed into collection chamber 74. The shoulder 83 is preferably tapered at an angle in the range of 10 to 30 degrees, depending on the French size of the atherectomy device.

The proximal most tip of shoulder 83 is tapered back to form a non-dulling cutter stopper surface 85. The shoulder 83 is sized and positioned such that a portion of cutter 22 other than cutting edge 23 will abut against stopper surface 85 to limit the distal movement of cutter 22. The taper of stopper surface 85 preferably substantially the same angle as the portion of cutter 22 with which it will mate to limit the distal movement of the cutter in order to prevent binding. By way of example, an appropriate taper angle would be in the range of 15 to 30 degrees.

The distal extremity of the balloon 97 is secured to the nose member 87 by suitable means such as nylon wire 32 which is wrapped into an annular recess 82. The nylon wire wrap is fastened in place by use of a suitable plastic such as cyanoacrylate. The proximal extremity of the balloon 97 is secured as previously discussed.

In addition to protecting the cutter edge and serving as a foundation for tying the balloon 97, cutter stopper 78 forms a good base for joining collection chamber 74 to cutter tube 77. Cutter stopper 78 has a smaller diameter than both collection chamber 74 and cutter tube 77, and is sized to be tightly received thereby. Thus, the proximal end of the cutter stopper is received by the distal extremity of cutter tube 77 and is bonded thereto. Any strong biocompatible adhesive may be used. The portion of cutter stopper 78 distal to rib 81 includes a plurality of annular grooves 84. The annular grooves enhance the bond between the cutter stopper 78 and the collection chamber 74.

Similarly, nose cone 87 includes a reduced diameter shoulder 88 having annular grooves 89 on its proximal side. Shoulder 88 and its annular grooves 89 function similarly to the portion of cutter stopper 78 located distally of rib 81, and facilitate attachment to collection chamber 74.

A coil spring 85 disposed within collection chamber 74 is attached on its opposite ends to nose cone 87 and cutter stopper 78, to provide an additional bond therebetween. This ensures that the nose cone 87 will not break loose while the device is in use. Further, the coil spring 85 provides additional support to flexible collection chamber 74 and reduces kinking. The coil spring 85 may be attached to nose cone 87 and cutter stopper 78 in any conventional fashion. By way of example, a suitable attachment could be formed by soldering opposite ends of the coil spring 85 to the nose cone 87 and cutter stopper 78 respectively. The coil spring 85 may be formed of any suitable material, such as stainless steel.

The flexible collection chamber 74 shown in FIG. 6 is of a braided type construction. It may be formed of a nylon plastic tube that is covered with braided fibers and sealed with a flexible epoxy or urethane. Alternatively, the collection chamber 74 could be fabricated using any of the alternative techniques previously described.

By way of example, collection chamber 74 may be formed of a suitable base material such as nylon or Teflon TM tubing having a thickness of approximately 1-3 mils. The extruded nylon is placed about an extended mandril. Braided fibers are then applied to the outer surface of the nylon extrusion tube. The braids may be formed of any suitable fiber materials. By way of example, stainless steel stands having a diameter ranging from 1 mil to 3 mils and preferably having a diameter of approximately 2 mils may be used. Alternatively, flat braid strands having cross sectional areas of 1 mil by 2 or 3 mils would be suitable. Thereafter, the stainless steel fibers can be coated with a flexible plastic such as epoxy or polyurethane. By way of example, a coat of Scotch Weld 2216 B/A Grey manufactured by 3M of St. Paul, Minn. may be used. After the epoxy has been applied, it is baked to harden. It may be necessary to apply several coats of epoxy in order to properly cover the braids. The composite tubing is then ground to the desired thickness and cut to length. The distal end of the flexible housing portion is then bonded to the nose piece while the proximal end is bonded to cutter stopper 78. The cutter tube 77 is then attached to the proximal end of the cutter stopper 78. After the housing 71 has been formed, it is attached to the distal extremity of tubular member 13, the cutter is moved into position and the balloon is tied in place.

From the foregoing it can be seen that the flexible housing lends itself to use in situations where very small diameter arterial vessels must be navigated by the atherectomy device. The flexible housing provided makes it possible for the device to follow the tortuousity of the small arterial vessels, as for example, those particularly associated with the heart.

Although only a few embodiments of the present invention have been described, it should be understood that the present invention may be embodied in many other specific forms without departing from the sphere or scope of the invention. Particularly, it should be appreciated that any of the housings described might be externally dip coated with a urethane coating to lower metal fatigue, or to fill slots within the housing. Additionally, the cutter stopper could be employed in any of the described embodiments to both preserve the cutting edge and to form a base for tying off the balloon. Therefore, the present examples and embodiments are to be considered as illustrative and not restrictive, and the invention is not to be limited to details given herein, but may be modified within the scope of the appended claims.

What is claimed is:

1. In an atherectomy device for use in a vessel, a flexible tubular member having proximal and distal ends and having at least one lumen extending therethrough, a housing secured to the distal end of the tubular member, the housing having a cutout in one side thereof extending longitudinally of the housing and facing outwardly in a direction which is generally perpendicular to the longitudinal axis of the housing, a collection chamber formed in the housing for retaining severed atheroma materials within the atherectomy device, a rotary cutter mounted in the housing for movement longitudinally of the housing through the cutout, at least a portion of the housing being flexible so as to permit bending of the housing between its distal and proximal extremities whereby the housing has the capability of following contours in a vessel in which the atherectomy device is to be utilized and, inflatable balloon means carried by the housing and mounted exterior of the housing on the side opposite the cutout so that when the balloon means is inflated the cutout will be moved towards the sidewall of the vessel.

2. A device as in claim 1 wherein said flexible portion of the housing houses the collection chamber.

3. A device as in claim 1 wherein said housing is substantially circular in cross section.

4. A device as in claim 1 wherein said flexible portion of said housing is formed of a braided material.

5. A device as in claim 4 wherein said braided material is impregnated with a plastic.

6. A device as in claim 1 wherein said flexible portion of the housing is formed of a rigid material having a plurality of arcuate cutouts disposed therein spaced apart longitudinally of the housing and extending at a substantial angle with respect to the longitudinal axis of the housing.

7. A device as in claim 6 wherein a plastic material is disposed in the cutouts in the housing.

8. A device as in claim 6 wherein the cutouts extend in a direction substantially perpendicular to the longitudinal axis of the housing.

9. In the atherectomy device for use in a vascular vessel, a flexible tubular member having proximal and distal ends and having at least one lumen running therethrough, the flexible tubular member being adapted for insertion into the vascular vessel, a housing carried by the distal extremity of the tubular member and having a cutout on one side thereof, the cutout extending longitudinally of the housing and facing outwardly in a direction that is generally perpendicular to the longitudinal axis of the housing, the housing having a collection chamber spaced distally of the cutout for retaining severed atheroma materials within the housing, a cutter rotatably mounted within the housing for movement longitudinally of the housing past the cutout, the cutter having an annular cutting edge, the portion of the housing containing the collection chamber being flexible so as to permit bending to allow the housing to follow contours in a vessel in which the atherectomy device is to be utilized.

10. An atherectomy device as in claim 9, wherein the portion of said housing having the cutout therein is rigid.

11. An atherectomy device as in claim 9, wherein said portion of the housing having the collection chamber therein is formed of a braided material.

12. An atherectomy device as in claim 9, wherein said flexible portion of the housing is formed of a flexible plastic tube encased by the braided material and wherein the braided material is sealed with a flexible material.

13. An atherectomy device as in claim 9, together with a nose cone coupled to the distal extremity of the collection chamber, and a flexible guide wire, secured to the nose cone and extending forwardly of the nose cone.

14. An atherectomy device as in claim 9 together with a cutter stopper that includes a shoulder having a diameter less than the diameter of the cutting edge, the shoulder being adapted to engage a portion of the cutter other than the cutting edge to limit the cutter's distal movement without contacting the cutting edge.

* * * * *